United States Patent [19]

Matsuda et al.

[11] Patent Number: 4,605,779

[45] Date of Patent: Aug. 12, 1986

[54] METHOD FOR THE PRODUCTION OF TIGLIC ALDEHYDE

[75] Inventors: Teruo Matsuda, Ehime; Shinkichi Shimizu, Osaka; Masaaki Iwasa, Ehime, all of Japan

[73] Assignee: Sumitomo Chemical Company, Limited, Osaka, Japan

[21] Appl. No.: 758,017

[22] Filed: Jul. 24, 1985

[30] Foreign Application Priority Data

Jul. 24, 1984 [JP] Japan .................................. 59-154635

[51] Int. Cl.$^4$ ............................................. C07C 45/67
[52] U.S. Cl. ................................................... 568/450
[58] Field of Search ......................... 568/450

[56] References Cited

U.S. PATENT DOCUMENTS

| | | | |
|---|---|---|---|
| 4,192,820 | 3/1980 | Meissner | 568/450 |
| 4,346,239 | 8/1982 | Back | 568/461 |
| 4,408,079 | 10/1983 | Merger et al. | 568/461 |

FOREIGN PATENT DOCUMENTS

| | | | |
|---|---|---|---|
| 0037584 | 10/1981 | European Pat. Off. | 568/450 |
| 2451923 | 5/1976 | Fed. Rep. of Germany | 568/450 |
| 2620967 | 11/1976 | Fed. Rep. of Germany | 568/450 |

*Primary Examiner*—Werren B. Lone
*Attorney, Agent, or Firm*—Sughrue, Mion, Zinn, Macpeak, and Seas

[57] ABSTRACT

A novel method for producing tiglic aldehyde from ethylacrolein by isomerization in the presence of a hydrogenating catalyst is disclosed. According to the invention, tiglic aldehyde can be prepared in a good yield.

3 Claims, No Drawings

METHOD FOR THE PRODUCTION OF TIGLIC ALDEHYDE

FIELD OF THE INVENTION

This invention relates to a novel method for the production of tiglic aldehyde [2-methyl-2-butene-1-al,

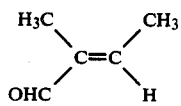

].

BACKGROUND OF THE INVENTION

Tiglic aldehyde is an important raw material for the synthesis of isoterpenes. Tiglic acid

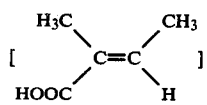

which is obtained by oxidation of tiglic aldehyde is useful as a raw material for the synthesis of driers for perfumes, varnishes, inks, and the like. Further, a chloride of tiglic aldehyde [4-chloro-2-methyl-2-butene-1-al,

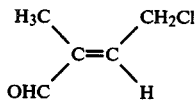

] is a useful compound to extend an isoterpene chain at one.

Hitherto, as a method for the production of tiglic aldehyde, a so-called Cross's aldol condensation method wherein acetaldehyde and propionaldehyde are condensed in a strong basic condition is known. However, this method has a drawback that the yield of said aldehyde is poor with a large quantity of various by-products being formed (see M. B. Green, W. T. Hickinbottom, *Journal of Chemical Society*, page 3262 (1975)).

With the purpose of producing tiglic aldehyde in a good yield from materials which are available at a low price, the present inventors have extensively investigated various synthesis routes thereof and achieved this invention.

SUMMARY OF THE INVENTION

An object of this invention is to provide a method for producing tiglic aldehyde which is an important raw material for the synthesis of isoterpenes.

Another object of this invention is to provide a method for producing tiglic aldehyde in a good yield from materials which are available at a low price.

Other objects and advantages of this invention will become apparent from the accompanying description and examples.

DETAILED DESCRIPTION OF THE INVENTION

This invention provides a method for the production of tiglic aldehyde, which comprises isomerizing ethylacrolein.

Ethylacrolein which is used as a starting material for the synthesis of tiglic aldehyde of this invention can be almost quantitatively prepared by condensing usual industrial materials, n-butylaldehyde and a formalin aqueous solution (see U.S. Pat. No. 4,346,239). The isomerization of ethylacrolein of this invention can be carried out by either a liquid phase reaction or a gas phase reaction.

When the liquid phase reaction is employed for the production of tiglic aldehyde, ethylacrolein is heated together with of a solvent and a catalyst. Examples of the solvent which can be used in this reaction include aromatic hydrocarbons, alcohols and aliphatic hydrocarbons. Illustrative of such solvents are toluene, ethylbenzene, xylene, n-butanol, n-octane and the like.

Examples of the catalyst which can be used in this reaction include metals belonging to the VIII group of the periodic table, such as platinum, palladium, rhodium and ruthenium. These metals are generally supported on a carrier such as an activated carbon or alumina for use. These supported catalysts are generally used as a hydrogenating catalyst and on the market, for example, are 5% palladium-on-carbon and 0.5% palladium-on-alumina made by Nippon Engel Hard Co., Ltd.

When the catalyst is poisoned by, for example, sodium dithionite, sulfonic acid, thiophene, thiourea, or 1,1,3,3-tetramethylthiourea, the reactivity reduces but the selectivity of the isomerization increases.

When hydrogen is copresent in the reaction system, though a saturated aldehyde, 2-methylbutanal

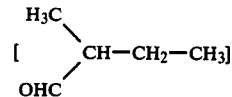

is formed as a by-product, the isomerization becomes extremely active, leading to an increase in yield.

The reaction temperature may be 50° C. or higher, but when the reaction temperature is too low, the rate of reaction is low, whereas when the reaction temperature is too high, a loss which may be caused by the polymerization occurs. Accordingly, preferable results can be obtained in the range of from 80° C. to 150° C.

The catalyst which was used can be repeatedly used ten times by mere filtration without any other treatment, and there was not found any change in reactivity.

On the other hand, the gas phase reaction can be conducted by either a fixed bed reaction or a fluidized bed reaction. That is, tiglic aldehyde can be prepared by passing vaporized ethylacrolein with a carrier gas through a catalyst layer under heating. In this case, as the carrier gas which can be used, any inactive gas can be used, and examples thereof include nitrogen gas, argon gas and a process-waste gas.

As the catalyst which can be used in this reaction, silica, alumina and silica-alumina can also be used in addition to the metals belonging to the VIII group of the periodic table (such as palladium, platinum, rhodium and ruthenium). Illustrative of catalysts which are commercially available are 0.5% palladium-on-allumina (made by Nippon Engel Hard Co., Ltd.) and silica-alumina N-631L (made by JGC Corporation).

When platinum-group metal-supported catalysts are used, the reaction temperature is relatively low as about 300° C. or lower, preferably from 50° to 150° C. When silica-alumina catalysts are used, the reaction temperature is relatively high as 200° C. to 400° C., preferably from 250° C. to 350° C. In both of the cases, a high yield can be attained.

In this case, a preferable space velocity is from 100 to 5000 hr$^{-1}$, most preferably from 500 to 2000 hr$^{-1}$.

A suitable molar ratio of the carrier gas to ethylacrolein is in the range of from 1/1 to 100/1, preferably from 10/1 to 50/1. When hydrogen is used as an activator, a suitable molar ratio of hydrogen to ethylacrolein is in the range from 0/1 to 1/1, preferably from 0/1 to 0.2/1. In this case, a high yield can be attained.

As stated above, according to the method for isomerization of ethylacrolein to tiglic aldehyde, tiglic aldehyde can be prepared in a good yield by using n-butylaldehyde and a formalin aqueous solution which are readily commercially available.

The following examples are further illustrative of this invention. The catalysts and other specific ingredients and processing parameters are presented as being typical, and various modifications can be derived in view of the foregoing disclosure within the scope of the invention.

EXAMPLE 1

In a stainless steel reactor having a capacity of 100 ml were placed 8.4 g of ethylacrolein (0.1 mol), 25 ml of ethylbenzene, and 0.3 g of catalyst 1. The reactor was purged with nitrogen, and 500 ml of hydrogen gas at standard condition was then introduced in the reactor. The mixture was heated at 100° C. for 6 hours.

After cooling the reactor, the reaction solution was analyzed by gas chromatography. The results of the reaction showed that the conversion of ethylacrolein was 97%, the yield of tiglic aldehyde was 74% and the yield of saturated aldehyde (2-methylbutane-1-al) was 22%.

The identification of the product obtained relied on mass analysis and NMR analysis.

EXAMPLES 2 TO 6

Using catalyst 1 or 2, the same procedures as in Example 1 were followed except changing the kind of the solvent (but not changing the amount (weight) of the solvent). The results are shown in Table 1.

TABLE 1

| Example No. | Solvent | Catalyst | Hydrogen (NTP) (ml) | Reaction Condition temperature (°C.) × time (hr) | Conversion of Ethylacrolein (%) | Yield of Tiglic Aldehyde (%) | Yield of Saturated Aldehyde (%) |
|---|---|---|---|---|---|---|---|
| 2 | toluene | catalyst 2 | 680 | 100 × 6 | 95 | 63 | 29 |
| 3 | methanol | catalyst 2 | 680 | 100 × 6 | 80 | 48 | 16 |
| 4 | n-butanol | catalyst 2 | 280 | 120 × 4 | 82 | 59 | 15 |
| 5 | n-octane | catalyst 2 | 280 | 120 × 4 | 79 | 63 | 14 |
| 6 | xylene | catalyst 1 | 400 | 100 × 6 | 85 | 67 | 18 |

PREPARATION OF CATALYSTS

Catalyst 1

0.052 g of sodium dithionite (Na$_2$S$_2$O$_4$) was dissolved in 100 ml of water, and 20.0 g of a 5% palladium-on-carbon powder (Nippon Engel Hard Co., Ltd.) was added thereto. The mixture was then stirred for 30 minutes.

EXAMPLE 7

The catalyst used in Example 1 was filtered and then reused. The reaction was carried out at 100° C. for 6 hours using 4.2 g of ethylacrolein, 12.5 ml of ethylbenzene, 0.15 g of recovered catalyst 1, and 250 ml of hydrogen gas. The results are shown in Table 2.

TABLE 2

| Solvent | Catalyst | Hydrogen (NTP) (ml) | Reaction Condition temperature (°C.) × time (hr) | Conversion of Ethylacrolein (%) | Yield of Tiglic Aldehyde (%) | Yield of Saturated Aldehyde (%) |
|---|---|---|---|---|---|---|
| ethylbenzene | catalyst 1 | 250 | 100 × 6 | 99 | 75 | 22 |

The mixture was heated on a sand bath to evaporate off water, and the residue was kept in a vacuum drying oven at 120° C. for 24 hours.

Catalyst 2

0.5 g of thiourea was dissolved in 300 ml of acetone, and 20 g of a 5% palladium-on-carbon powder (Nippon Engel Hard Co., Ltd.) was added thereto. The mixture was then stirred for 30 minutes. The acetone was evaporated off by a rotary evaporator, and the residue was kept in a vacuum drying oven at 120° C. for 12 hours.

Catalyst 3

0.4 g of thiophene was dissolved in 300 ml of acetone, and 20 g of a 5% palladium-on-carbon powder was added thereto. The mixture was then stirred at room temperature for 30 minutes. The acetone was evaporated off by a rotary evaporatoe, and the residue was kept in a vacuum drying oven at 120° C. for 12 hours.

EXAMPLE 8

In a glass reactor equipped with a reflux condenser were placed 25 ml of toluene and 8.4 g of ethylacrolein, the reactor was purged with nitrogen, and 0.3 g of catalyst 3 was then added thereto. The mixture was refluxed under heating for about 6 hours while supplying a 5% hydrogen gas (the balance being nitrogen) into the reactor at a flow rate of 30 ml/min. The results are shown in Table 3.

TABLE 3

| Reaction Time (hr) | Conversion of Ethylacrolein (%) | Yield of Tiglic Aldehyde (%) | Yield of 2-Methylbutane-1-al (%) |
|---|---|---|---|
| 6 | 49 | 39 | 7 |

EXAMPLE 9

In a glass reactor was packed 2 g of a 5% palladium-on-alumina tablet, and ethylacrolein, hydrogen and nitrogen were introduced thereinto at a ratio of 1/0.037/3.4 in the gas phase. The yield of tiglic aldehyde was 35% at a space velocity (SV) of 700 hr$^{-1}$ and at 100° C.

EXAMPLE 10

The catalyst used in Example 9 was used as it was but the introduction of the hydrogen was not carried out. As the result, the reaction at 150° C. afforded tiglic aldehyde in a yield of 36%.

EXAMPLE 11

A silica-alumina catalyst (N-631L, made by JGC Corporation) was used under the same condition as in Example 9. As the result, the reaction at 300° C. afforded tiglic aldehyde in a yield of 10%.

While the invention has been described in detail and with reference to specific embodiments thereof, it will be apparent to one skilled in the art that various changes and modifications can be made therein without departing from the spirit and scope thereof.

What is claimed is:

1. A process for producing tiglic aldehyde of the formula:

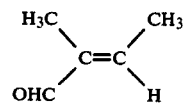

which comprises isomerizing ethylacrolein at a temperature in the range of from 50° C. to 150° C. and in the presence of hydrogen gas in an amount of from 0 to 1 mole per mole of said ethylacrolein and at least one hydrogenating catalyst selected from the group consisting of palladium, platinum, rhodium and ruthenium.

2. A process in accordance with claim 1, wherein the reaction is carried out in a liquid phase in the presence of at least one hydrogenating catalyst selected from the group consisting of palladium, platinum, rhodium and ruthenium.

3. A process in accordance with claim 1, wherein the reaction is carried out in a gas phase.

* * * * *